United States Patent
Simó Canonge et al.

(10) Patent No.: US 9,216,208 B2
(45) Date of Patent: Dec. 22, 2015

(54) TOPICAL OPHTHALMIC PEPTIDE FORMULATION

(75) Inventors: Rafael Simó Canonge, Barcelona (ES); Cristina Hernández Pascual, Barcelona (ES); Jimena Fernández Carneado, Villaviciosa-Asturias (ES); Marc Gómez Caminals, Barcelona (ES); Rlbera Jordana I Lluch, Barcelona (ES); Josep Farrera Sinfreu, Tirvia (ES); Berta Ponsati Obiols, Barcelona (ES)

(73) Assignee: BCN Peptides, S.A., Barcelona (ES)

( * ) Notice: Subject to any disclaimer, the term of this patent is extended or adjusted under 35 U.S.C. 154(b) by 0 days.

(21) Appl. No.: 13/518,617

(22) PCT Filed: Dec. 17, 2010

(86) PCT No.: PCT/EP2010/007737
§ 371 (c)(1),
(2), (4) Date: Aug. 20, 2012

(87) PCT Pub. No.: WO2011/076368
PCT Pub. Date: Jun. 30, 2011

(65) Prior Publication Data
US 2013/0210728 A1 Aug. 15, 2013

(30) Foreign Application Priority Data
Dec. 23, 2009 (ES) .................................. 200931242

(51) Int. Cl.
| A61K 9/127 | (2006.01) |
| A61K 9/00 | (2006.01) |
| A61K 38/00 | (2006.01) |
| A61K 38/31 | (2006.01) |
| A61K 47/48 | (2006.01) |
| A61K 9/51 | (2006.01) |
| A61K 9/08 | (2006.01) |
| A61K 47/02 | (2006.01) |

(52) U.S. Cl.
CPC ............... *A61K 38/31* (2013.01); *A61K 9/0048* (2013.01); *A61K 9/127* (2013.01); *A61K 9/5153* (2013.01); *A61K 47/48023* (2013.01); *A61K 47/48215* (2013.01); *A61K 9/08* (2013.01); *A61K 47/02* (2013.01)

(58) Field of Classification Search
None
See application file for complete search history.

(56) References Cited

U.S. PATENT DOCUMENTS

| 5,182,258 A | 1/1993 | Chiou |
| 2002/0142944 A1 | 10/2002 | Kuijpers et al. |
| 2004/0037889 A1 | 2/2004 | Richeal et al. |
| 2004/0219205 A1 | 11/2004 | Kan et al. |
| 2005/0074497 A1 | 4/2005 | Schultz |
| 2006/0228414 A1 | 10/2006 | Cook |

FOREIGN PATENT DOCUMENTS

| EP | 1040837 | | 10/2000 |
| EP | 1040837 A2 | * | 10/2000 |
| EP | 2052716 | | 4/2009 |
| WO | 9924019 | | 5/1999 |
| WO | 0209739 | | 2/2002 |
| WO | WO 0209739 A1 | * | 2/2002 |
| WO | 2005009356 | | 2/2005 |
| WO | WO 2005009356 A2 | * | 2/2005 |
| WO | WO 2007038687 A2 | * | 4/2007 |
| WO | WO 2009040035 A2 | * | 4/2009 |

OTHER PUBLICATIONS

Le Bourlais et al., "Ophthalmic drug delivery systems—recent advances," Progress Retinal Eye Res. 17:33-58 (1998).*
Hartong et al., "Retinitis pigmentosa," Lancet 368:1795-1809 (2006).*
Emerson et al., "Emerging therapies for the treatment of neovascular age-related macular degeneration and diabetic macular edema," Biodrugs 21:245-257 (2007).*
International Search Report for PCT/EP2010/007737, Completed by the European Patent Office on Jan. 10, 2012, 4 Pages.
Minsel et al. Endocrinology May 2009, vol. 150, No. 5, p. 2254-2263, "Somatostatin Actions via Somatostatin Receptors on the Ocular Surface Are Modelated bu Inflammatory Process."
Akyol et al. Graefe's Arch Clin Exp Ophthalmol 2003, vol. 241, p. 816-822, "Ciliary body toxicity of cyclosporin A and octreotide acetate in rabbit eyes: a comparison with mitomycin C and 5-fluorouracil."
Klisovic et al. Investigative Ophthalmology and Visual Science Sep. 2001, vol. 42, No. 10, p. 2193-2201, "Somatostatin Receptor Gene Expression in Human Ocular Tissues: RT-PCR and Immunogistochemical Study."
Palii et al. Investigative Ophthalmology and Visual Science Nov. 2008, vol. 49, No. 11, p. 5094-5102, "Nonpeptide Somatostatin Receptor Agonists Specifically Target Ocular Neovascularization via the Somatostatin Type 2 Receptor."
Geroski et al. Investigative Ophthalmology and Visual Science Apr. 2000, vol. 41, No. 5, p. 961-964, "Drug Delivery for Posterior Segment Eye Disease."
Kiagiadaki et al. Investigative Ophthalmology and Visual Science Jul. 2008, vol. 49, No. 7, p. 3080-3089, "Effect of Intravitreal Administration of Somatostatin and sst2 Analogs on AMPA-Induced Neurotoxicity in Rat Retina."
Hancock et al. Investigative Ophthalmology and Visual Science Mar. 2004, vol. 45, No. 3, p. 1002-1008, "Oscillatory Potential Analysis and ERGs of Normal and Diabetic Rats."
Van Hagen et al. European Journal of Endocrinology 2000, vol. 143, p. S43-S51, "Somatostatin and somatostatin receptors in retinal diseases."

(Continued)

*Primary Examiner* — Julie Ha
*Assistant Examiner* — Kristina M Hellman
(74) *Attorney, Agent, or Firm* — Brooks Kushman P.C.

(57) ABSTRACT

A topical ophthalmic formulation of peptides and their use for the treatment and/or local prevention of ocular diseases, preferably posterior segment eye diseases.

9 Claims, 3 Drawing Sheets

(56) References Cited

OTHER PUBLICATIONS

Simo et al. Diabetes Care Dec. 2002, vol. 25, No. 12, p. 2282-2286, "Deficit of Somatostatin0Like Immunoreactivity in the Vitreous Fluid of Diabetic Patients."

Danesi et al. Clin Cancer Res 1997, vol. 3, p. 265-272, "Inhibition of experimental angiogenesis by the somatostatin analogue octreotide acetate (SMS 201-995)."

Cervia et al. Molecular and Cellular Endocrinology 2008, vol. 286, p. 112-122, "Physiology and pathology of somatostatin in the mammalian retina: a current view."

Wegewitz et al. Current Pharmaceutical Design 2005, vol. 11, p. 2311-2330, "Novel Approaches in the Treatment of Anagiogenic Eye Disease."

Herrero-Vanrell et al. J. Drug Del. Sci. Tech. 2007, vol. 17, No. 1, p. 11-17, "PLA and PLGA microparticles for intravitreal drug delivery: an overview."

Robertson et al. Journal of Ocular Pharmacology and Therapeutics 1997, vol. 13, No. 2, p. 171-177, "Intravitreal Injection of Octreotide Acetate."

Demir et al. Documenta Opthalmologica 2003, vol. 107, p. 87-92, "Effects of actreotide acetate and amniotic emebrane on wound healing in experimental glaucoma surgery."

Tzekov et al. Survey of Ophthalmology Jul.-Aug. 1999, vol. 44, No. 1, p. 53-60, "The Electroretinogram in Diabetic Retinopathy."

Carrasco et al. Diabetes Care Nov. 2007, vol. 30, No. 11, p. 1-7, "Lower Somatostatin Expression is an Early Event in Diabetic Retinipathy and is Associated With Retinal Neurodegeneration."

Guerrero et al. Arch Soc Esp Oftalmol 2008, vol. 83, p. 683-686, English translation attahced to original, "Ocular Drug Absorption by Topical Route. Role of Conjunctiva."

del Amo, E.M. et al., "Current and Future Ophthalmic Drug Delivery Systems A Shift to the Posterior Segment," Drug Discovery Today, v. 13, Nos. 3/4, Feb. 2008, pp. 135-143.

Grant, M.B. et al., "The Efficacy of Octreotide in the Therapy of Severe Nonproliferative and Early Proliferative Diabetic Retinopathy," Diabetes Care, v. 23, No. 4, Apr. 2000, pp. 504-509.

Hernández, C. et al., "Topical Administration of Somatostatin Prevents Retinal Neurodegeneration in Experimental Diabetes," Diabetes, v. 62, Jul. 2013, pp. 2569-2578.

Higgins, R.D. et al., "Somatostatin Analogs Inhibit Neonatal Retinal Neovascularization," Exp. Eye Res. (2002) 74, pp. 553-539.

Kuijpers, R.W. et al., "Treatment of Cystoid Macular Edema with Octreotide," The New England Journal of Medicine, Feb. 26, 1998, pp. 624-626.

McCombe, M. et al., "Effect of a Long-Acting Somatostatin Analogue (BIM23014) on Proliferative Diabetic Retinopathy: A Pilot Study," Eye (1991) 5, pp. 569-575.

Raghava, S. et al., "Periocular Routes for Retinal Drug Delivery," Expert Opin. Drug Deliv. (2004) 1(1), pp. 99-114.

Read, R.W., "Uveitis: Advances in Understanding of Pathogenesis and Treatment," Current Rheumatology Reports, 2006, 8, pp. 260-266.

Smith, L. E. H. et al., "Essential Role of Growth Hormone in Ischemia-Induced Retinal Neovascularization," Science, v. 276, Jun. 13, 1997, pp. 1706-1709.

Van Hagen, P.M. et al., "Somatostatin and Somatostatin Receptors in Retinal Diseases," European J. of Endocrinology, (2000) 143, pp. S43-S51.

Urto, A., "Challenges and obstacles of ocular pharmacokinetics and drug delivery," Advanced Drug Delivery Reviews 58 (2006), pp. 1131-1135.

* cited by examiner

TOPICAL OPHTHALMIC PEPTIDE FORMULATION

CROSS-REFERENCE TO RELATED APPLICATION

This application is the U.S. national phase of PCT Appln. No. PCT/EP2010/007737 filed on 17 Dec. 2010, which claims priority to Spanish Patent Application No. P 200931242 filed on 23 Dec. 2009, the disclosures of which are incorporated in their entirety by reference herein.

FIELD OF THE INVENTION

This invention belongs to the field of medicine, and in particular it relates to a pharmaceutical formulation in the form of a topical ophthalmic composition of somatostatin and somatostatin analogues.

BACKGROUND OF THE INVENTION

Diseases of the retina and vitreous body are the principle causes of blindness, and among them are outstanding diabetic retinopathy and age-related macular degeneration.

Although there are references in the prior art of the potential use of somatostatin and analogues in the treatment of posterior segment eye diseases, based on the evidence of the overexpression of somatostatin receptors in these disorders, there are no clear examples of therapeutic effect.

The presence of endogenous somatostatin and somatostatin receptors in the different parts of the human eye has recently been described. Therefore, for example, the somatostatin receptors sstr1, sstr2 and sstr5 have been detected in the lacrimal glands, conjunctiva, cornea and nasolacrimal ducts [Minsel et al., *Endocrinology*, 2009, 150(5): 2254-2263]. In the posterior segment of the eye the presence of genes corresponding to the somatostatin receptors sstr1, sstr2, sstr3, sstr4 and sstr5 in the retina, ciliary body and choroids in healthy human eyes have been described [Klisovic et al., *Investigative Ophthalmology & Visual Science*, 2001, 42(10): 2193-2201], the presence of sstr2 and sstr3 mRNA in the retina [van Hagen et al., *European Journal of Endocrinology*, 2000, 143: S43-S51; Cervia et al., *Molecular and Cellular Endocrinology*, 2008, 286: 112-122] and also the presence of endogenous somatostatin in the vitreous humor and the retina [Simó et al., *Diabetes Care*, 2002, 25(12): 2282-2286]. It is also known in the prior art that there is a lower expression of somatostatin in the retina in the first phases of diabetic retinopathy, possibly associated to retinal neurodegeneration [Carrasco et al., *Diabetes Care*, 2007, 30(11): 1-7].

There are different routes of administration of drugs for the treatment of posterior segment eye diseases such as systemic, topical, intraocular and periocular administration.

Document WO 02/09739 A1 describes the use of somatostatin or an analogue thereof for the treatment or prevention of ocular disorders. Among the routes of administration named in this document, the preferred route is systemic parenteral administration, subcutaneous or intramuscular, and there is no indication in said document of a formulation in the form of eye-drops for the administration of somatostatin or an analogue of it. However, in the case of systemic administration it is difficult to reach therapeutic concentrations in the posterior segment of the eye due to the hemato-retinal barrier, which limits the penetration of medication into the eye. Another general disadvantage of systemic administration is that its effect is not local and it is not directed exclusively to the posterior segment of the eye. Furthermore, in the case of somatostatin, high doses would be necessary due to its instability in blood. In the case of the analogue octreotide, different clinical studies have assessed its effects through systemic subcutaneous administration, even if the results do not show a clear therapeutic effect [Wegewitz et al., *Current Pharmaceutical Design*, 2005, 11: 2311-2330; Palif et al., *Investigative Ophthalmology & Visual Science*, 2008, 49(11): 5094-5102].

An alternative to the low availability of the systemic route of administration in the posterior segment of the eye is the local administration in the posterior segment of the eye through intraocular injections and periocular injections such as subconjunctival, sub-Tenon and retrobulbar injections, or subconjunctival implants in this segment [Geroski et al., *Investigative Ophthalmology & Visual Science*, 2000, 41(5): 961-964; Kiagiadaki et al. *Investigative Ophthalmology & Visual Science*, 2008, 49(7): 3080-3089]. However, these forms of administration are not comfortable for the patient and present secondary effects whose frequency increases if they are carried out repeatedly. Furthermore, in the case of implants, they entail a surgical intervention. Although these type of treatments have shown to be effective in preclinical studies, they require the regular application of injections which in some cases have secondary effects such as retinal detachment, cataracts, rubeosis or endophthalmitis [Geroski et al., *Investigative Ophthalmology & Visual Science*, 2000, 41(5): 961-964; Herrero-Vanrell et al, *Journal of Drug Delivery Science and Technology*, 2007, 17(1): 11-17; Robertson et al., *Journal of Ocular Pharmacology and Therapeutics*, 1997, 13(2): 171-177].

Another alternative to the previous routes of administration of drugs to the eye is topical ocular administration. However, the topical ocular channel, as a route of administration of medication whose target is in the posterior segment of the eye, has been limited up until now due to the estimation that the percentage of active substance capable of reaching the posterior segment is insignificant in the majority of cases. [Andrés-Guerrero et al., *Archivos de la Sociedad Española de Oftalmologia*, 2008, 83: 683-686].

Within the prior art several options for topical ocular administration of somatostatin and analogues have been mentioned. Therefore, for example, document US 2005/074497 A1 describes a hydrogel which contains an anti-angiogenic drug, such as octreotide, for the treatment of posterior segment eye disease. Octreotide is disclosed in this patent application inside of a vast list of drugs. Furthermore, no example of octreotide or any other drug is described in this document. The hydrogel is placed in contact with the eye by using a contact lens or alternatively it is attached to the eye using adhesives or by surgical intervention. Administration by eye drops is explicitly excluded in this document. However, administration using a contact lens entails the risk of the eye becoming infected by pathogens and additionally, it is not tolerated by patients with increased intraocular pressure.

Another possibility is topical administration in the form of an ointment or unguent in the inner part of the eyelid. However, ointments tend to be uncomfortable and lower visual acuity due to their excessive viscosity and slow absorption.

Document WO 99/24019 A1 also describes a dry, solid formulation made of different drugs, among them somatostatin, which is reconstituted in a liquid solution and is administered as ophthalmic drops. Although this document does not provide any example of a formulation of somatostatin, nor any indication of this or another drug which reaches the posterior segment of the eye applied using eye drops.

On the other hand, document U.S. Pat. No. 5,182,258 A describes a formulation in the form of eye drops which, through the nasolacrimal system, is used for systemic administration, where the active principle being administered can be somatostatin, among many others. However, nothing is said in this document about the administration of this or another active principle for the treatment of posterior segment eye disease. The same occurs for other formulations in the prior art where octreotide is administered by topical route without a possible application for the treatment and/or prevention of posterior segment eye diseases being indicated [Danesi et al., *Clinical Cancer Research*, 1997, 3: 265-272; Demir et al. *Documenta Ophthalmologica*, 2003, 107: 87-92].

Therefore, there is in the prior art the need to find a form of topical ocular administration of somatostatin or an analogue thereof for the local treatment and/or prevention of posterior segment eye diseases which resolves both the problems of comfort for the patient and low therapeutic availability in a pharmaceutically acceptable formulation.

The object of this invention is a topical ophthalmic composition, a liquid pharmaceutical formulation which is administered topically in the eye, of somatostatin or an analogue thereof, which reaches the posterior segment of the eye, joins the somatostatin receptors present there and which is applied for the treatment and/or prevention of posterior segment eye diseases which benefit from the binding of somatostatin or its analogues to the somatostatin receptors. This invention provides an unprecedented breakthrough in the topical ophthalmic administration of peptides, and particularly, somatostatin or its analogues.

DESCRIPTION OF THE INVENTION

Surprisingly, this invention resolves the previously described problems. In a first aspect, this invention relates to a topical ophthalmic composition which contains a peptide characterized in that a therapeutically effective amount of this peptide reaches the posterior segment of the eye. In a particular embodiment, the topical ophthalmic composition is selected from the group of eye drops, ointments and unguents. In a further aspect, this invention relates to eye drops which contain a peptide characterized in that a therapeutically effective quantity of this peptide reaches the posterior segment of the eye.

In the context of this invention the term "eye drop" relates to a pharmaceutical liquid formulation which is administered in the form of drops on the external surface of the eye and which has a local effect on the posterior segment of the eye.

In the context of this invention the term "posterior segment of the eye" includes choroids, retinal pigment epithelium, retina, macula, fovea, optic nerve and vitreous humor.

In a particular embodiment, the peptide is selected from among somatostatin or a somatostatin analogue, preferably somatostatin or the somatostatin analogue are selected from the group formed by somatostatin-28, somatostatin-14, somatostatin-13, prosomatostatin, octreotide, lanreotide, vapreotide, pasireotide, seglitide, cortistatin and their pharmaceutically acceptable salts.

In another particular embodiment, somatostatin or the somatostatin analogue is substituted with an acyl group or a polyethylene glycol moiety. Preferably, the acyl group is selected from the group consisting of acetyl, tert-butanoyl, hexanoyl, 2-methylhexanoyl, cyclohexancarboxyl, octanoyl, decanoyl, lauroyl, myristoyl, palmitoyl, stearoyl, oleoyl and linoleoyl. Preferably, the polyethylene glycol moiety has a molecular weight between 200 and 35,000 daltons.

In another particular embodiment, the concentration of the peptide, preferably somatostatin or a somatostatin analogue, is between 0.1 µg/mL and 100 mg/mL, preferably, between 1 µg/mL and 10 mg/mL, more preferably between 10 µg/mL and 1 mg/mL.

In another particular embodiment, the pH of the eye drops is between 3 and 8, preferably between 4 and 7. To adjust the pH of the eye drops the acids and/or bases known by the person skilled in the art will be added to reach the previous pH values.

In another particular embodiment, the eye drop vehicle in the invention is an isotonic aqueous solution, such as the isotonic solution of sodium chloride or boric acid, or is a poly(vinyl alcohol) aqueous solution or mixtures thereof.

In another particular embodiment, the peptide of the composition of the invention can also be incorporated in liposomes, mixed liposomes, niosomes, ethosomes, nanoparticles, solid lipid nanoparticles, nanostructured lipid carriers, micelles, mixed micelles of surfactants, surfactant-phospholipid mixed micelles, nanospheres, liposphere and nanocapsules.

In another particular embodiment, the eye drops of this invention can optionally contain a preservative. A person skilled in the art recognizes the preservative agents of the prior art such as benzalkonium chloride, benzoic acid, alkyl parabens, alkyl benzoates, chlorobutanol, chlorocresol, cetyl alcohols, fatty alcohols such as hexadecyl alcohol, organometallic compounds of mercury such as acetate, phenylmercury nitrate or borate, diazolidinyl urea, diisopropyl adipate, dimethyl polysiloxane, salts of EDTA, vitamin E and its mixtures.

In another particular embodiment, the eye drops of this invention can optionally contain an agent which increases the permeability of the peptide, preferably of the peptide somatostatin or a somatostatin analogue, to the posterior segment of the eye. Preferably the agent which increases the permeability is selected from the group formed by benzalkonium chloride, saponins, fatty acids, polyoxyethylene fatty ethers, alkyl esters of fatty acids, pyrrolidones, polyvinylpyrrolidone, pyruvic acids, pyroglutamic acids and their mixtures, among others.

In a second aspect, this invention relates to the eye drops of this invention for the treatment and/or prevention of posterior segment eye diseases. Preferably, the treatment and/or prevention of the posterior segment eye disease benefit from the binding of somatostatin or its analogues to the somatostatin receptors. More preferably, the posterior segment eye disease are selected from the group formed by non-proliferative diabetic retinopathy, proliferative diabetic retinopathy, age-related macular degeneration, neovascular retinal disease, ischemia-induced retinopathy, retinopathy of prematurity, sickle-cell retinopathy, retinal vein occlusion, retinitis pigmentosa, choroidal neovascularization, uveitis, macular edema, cystoid macular edema. In the case of somatostatin, its greater stability in the vitreous humor of the posterior segment of the eye with regards to its half-life time in serum favors its action at a local level for the treatment and/or prevention of the previously mentioned posterior segment eye diseases.

In a third aspect, the present invention relates to a method of treatment and/or prevention of posterior segment eye diseases which comprises the topical administration of a therapeutically effective amount of a peptide by means of a topical ophthalmic composition selected from the group consisting of eye drops, ointments and unguents.

In a particular embodiment, the peptide is selected from among somatostatin or a somatostatin analogue, preferably somatostatin or the somatostatin analogue are selected from the group formed by somatostatin-28, somatostatin-14, somatostatin-13, prosomatostatin, octreotide, lanreotide, vapreotide, pasireotide, seglitide, cortistatin and their pharmaceutically acceptable salts.

In another particular embodiment, the frequency of administration can vary greatly, depending on the needs of each subject and the severity of the disease to be treated or prevented, with a recommendation of an administration range from once a week to ten times a day, preferably from three times a week to three times a day, even more preferably once or twice a day.

In another particular embodiment, the method of treatment and/or prevention additionally comprises the administration of another therapeutic agent for the treatment and/or prevention of posterior segment eye diseases. Therapeutic agents for the treatment and/or prevention of the posterior segment eye diseases are for example, and in a non-limiting sense, those agents selected from the group of anti-Vascular Endothelial Growth Factors (VEGF), prostaglandin analogs, beta-adrenergic receptor antagonists, alpha-2-adrenergic agonists, carbonic anhydrase inhibitors, miotic agents, monoclonal antibodies, corticosteroids, glucocorticoid, kinase inhibitors, cycloplegics or antimetabolites. The administration of these therapeutic agents for the treatment and/or prevention of posterior segment eye diseases can be by topical, oral or parenteral route. In the context of this invention, the term "parenteral" includes intravitreous, intraocular, intracorneal, subcutaneous, intradermal, intravascular injections, such as intravenous, intramuscular and any another similar injection or infusion technique.

The following specific examples given here serve to illustrate the nature of this invention. These examples are included solely for illustrative purposes and should not be interpreted as limitations to the invention claimed herein.

EXAMPLES

Example 1

Eye Drops which Contain Somatostatin-14

A pharmaceutical composition of somatostatin was prepared in the form of eye drops by adding 125 μL of 0.9% sodium chloride to 5 mg of somatostatin-14.

Example 2

Figure 1:
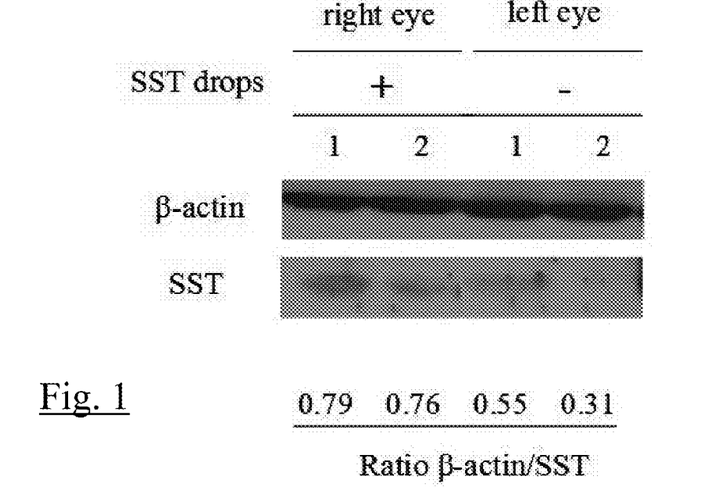
FIG. 1 shows the retinas of 2 mice (1 and 2) who received somatostatin in the right eye (+) and placebo in the left eye (−)

Evaluation of the Concentration of Topical Ophthalmic Somatostatin in the Retina Eight-week old C57BL/6 mice were used. The handling and care of the animals was carried out following the Institut de Recerca del Hospital Universitari Vall d'Hebron protocol and the European Economic Community and A.R.V.O. (Association for Research in Vision and Opthalmology) international guidelines (order 86/609/CEE). The animals were kept in individual cages in the animal facilities at a controlled temperature (20°) and humidity (60%), under constant cycles of light-darkness which last 12 hours and had free access to food and drink. The eye drops of somatostatin-14 from example 1 (1 drop of 5 μL) were administered to the right eye and the placebo (saline solution) to the left eye. Two drops were administered per day, one in the morning and another in the evening, for 5 days. The animals were euthanized by cervical dislocation under anesthetic 2 hours after the last dosage. Immediately afterwards the eyeballs were extracted and were frozen at −80° until handling. The posterior segment (retina and vitreous humor) was separated from the rest of the eyeball by dissecting it under a magnifying glass. The quantity of somatostatin-14 in the retina was determined by Western blot. The proteins were extracted with the solution 50 mM Tris-HCl, pH 7.9, 300 mM KCl, 1.5 mM $MgCl_2$, 0.1% Nonidet P-40 and 20% glycerol which contained Complete™ protease inhibitor cocktail at 4° C. for 12 hours. Subsequently the samples were centrifuged (12,000 rpm at 4° C.) for 10 min. A Western blot was carried out on the proteins with rabbit antibodies against somatostatin-14 (ab53165, abeam). To standardize the concentration of somatostatin-14 obtained □-actin was used as a control. The specific antibody-antigen complexes were identified using goat antibodies against rabbit IgG marked with HRP or rabbit antibodies against goat IgG together with chemiluminescent substrates (Pierce Biotechnology Inc., Rockfort, Ill., USA) by exposure on radiographic films. A densitometric analysis was carried out (Densitometer GS-800. Bio-Rad. Laboratories, Hercules, Calif., USA) and the results are expressed as arbitrary units. FIG. 1 shows the retinas of 2 mice (1 and 2) who received somatostatin in the right eye (+) and placebo in the left eye (−). As can be seen the amount of somatostatin was greater in the treated eye on both animals. On control mice, who received the placebo in both eyes, no differences were detected in the concentration of somatostatin between both eyes.

Example 3

Stability of Somatostatin in Human Vitreous Humor and Human Serum

Somatostatin was incubated with human serum or human vitreous humor at 90% at 37° C. Aliquots were extracted at different incubation times. Acetonitrile was added to precipitate the serum proteins, it was centrifuged and the supernatant was filtered and injected into the RP-HPLC (Gradient: 20-80% B in 30 min, B=0.07% TFA in acetonitrile). The disappearance of the initial product was analyzed using the area corresponding to the initial, product and the half-life time was calculated. The half-life time of somatostatin is 2.7 hours in serum and 64 hours in vitreous humor.

Example 4

Eye Drops which Contain Somatostatin-14

A pharmaceutical composition of somatostatin was prepared in the form of eye drops by adding 1 mL of 0.9% sodium chloride aqueous solution to 10 mg of somatostatin-14. Finally, the solution was filtered through a 0.22 μm sterilizing filter.

Example 5

Eye Drops which Contain Octreotide

A pharmaceutical composition of octreotide was prepared in the form of eye drops by adding 1 mL of 0.9% sodium chloride aqueous solution to 10 mg of octreotide. Finally, the solution was filtered through a 0.22 μm sterilizing filter.

Example 6

Eye Drops which Contain Vapreotide

A pharmaceutical composition of vapreotide was prepared in the form of eye drops by adding 1 mL of 0.9% sodium chloride aqueous solution to 10 mg of vapreotide. Finally, the solution was filtered through a 0.22 μm sterilizing filter.

Example 7

Eye Drops which Contain Cortistatin

A pharmaceutical composition of cortistatin was prepared in the form of eye drops by adding 1 mL of 0.9% sodium chloride aqueous solution to 10 mg of cortistatin. Finally, the solution was filtered through a 0.22 μm sterilizing filter.

Example 8

Eye Drops which Contain Somatostatin-14

A pharmaceutical composition of somatostatin was prepared in the form of eye drops by adding 1 mL of 0.9% sodium chloride and 1.4% poly(vinyl alcohol) aqueous solution to 0.27 mg of somatostatin-14. Finally, the solution was filtered through a 0.22 μm sterilizing filter.

Example 9

Eye Drops which Contain Somatostatin-28

A pharmaceutical composition of somatostatin was prepared in the form of eye drops by adding 1 mL of 0.9% sodium chloride aqueous solution to 0.05 mg of somatostatin-28. Finally, the solution was filtered through a 0.22 μm sterilizing filter.

Example 10

Eye Drops which Contain Somatostatin-14, Hydroxybenzoates and Polyoxyethylene Fatty Ethers A pharmaceutical composition of somatostatin was prepared in the form of eye drops by adding 1 mL of 0.9% sodium chloride aqueous solution to 50 μg of methyl 4-hydroxybenzoate, 100 μg of propyl 4-hydroxybenzoate, 50 μg of polyoxyethylene-20-stearyl ether (Brij-78) and 1 mg of somatostatin-14. Finally, the solution was filtered through a 0.22 μm sterilizing filter.

Example 11

Eye Drops which Contain Liposomes of Somatostatin-14

A pharmaceutical composition of somatostatin was prepared in 0.9% sodium chloride containing 20 mg of phosphatidyl choline and 2.7 mg of somatostatin-14 per mL. Briefly, phosphatidyl choline was slowly added under stirring to the 0.9% sodium chloride aqueous solution containing somatostatin-14. The composition was further stirred for 15 minutes until a liposome suspension was formed. Then liposomes were stepwise extruded through a polycarbonate filter with a 400 nm pore size, a 200 nm pore size filter and eventually ten times with a 100 nm pore size filter. Finally, the liposomal solution was filtered through a 0.22 μm sterilizing filter.

Example 12

Eye Drops which Contain Nanocapsules of Somatostatin-14

A 10% solution of poly lactic-co-glycolic acid (50:50) copolymer molecular weight 5000, 1 g, in dichloromethane was prepared. Somatostatin-14 (100 mg) was dissolved in 1 mL of water. The somatostatin solution was added to the polymer solution and was emulsified using one ultrasound probe. Then, the nanoemulsion was filtered through a 0.22 μm sterilizing filter. The resulting nanoemulsion was then dispersed in poly(vinylalcohol) 1% aqueous solution using ultrasound probe to reduce particle size until a nanoemulsion was obtained. The nanocapsules were extracted in a 40% ethanol aqueous solution and they were purified by tangential flow ultrafiltration.

Finally, 70 mg of nanocapsules containing somatostatin (16 mg) were dispersed in 100 mL poly(vinyl alcohol) 1.4% aqueous solution.

Example 13

Ophthalmic Ointment which Contains Somatostatin-14

A pharmaceutical composition of somatostatin was prepared in the form of ophthalmic ointment by adding 50 mL of white petrolatum USP to 200 mg of somatostatin-14.

Example 14

Effect of a Topical Ocular Treatment with Somatostatin and Octreotide in the Prevention of Retinal Neurodegeneration in Diabetic Rats Streptozotocin (STZ), 60 mg/Kg, was administered to Sprague Dawley rats. The animals were divided in four groups as detailed in Table 1:

TABLE 1

Study design

| Group/Identification | STZ Dose Level (mg/kg) | Treatment dose Drops in Right eye per day | Treatment dose Drops in Left eye per day | |
|---|---|---|---|---|
| 1/Vehicle | 0 | 1 | 2 | 4 |
| 2/STZ + Vehicle | 60 | 1 | 2 | 4 |
| 3/STZ + Somatostatin | 60 | 1 | 2 | 8 |
| 4/STZ + Octreotide | 60 | 1 | 2 | 8 |

(Vehicle = aqueous solution 0.9% NaCl)

Two days after STZ was administered, animals were treated daily with one or two drops of vehicle (Group 2), eye drops of example 4 (Group 3) or eye drops of example 5 (Group 4) for additionally 14 days. Healthy control animals were only treated daily with one or two drops of vehicle (Group 1).

Electroretinography is a technique used clinically to evaluate retinal function in diabetic retinopathy. Several parameters can be affected in early stages of the disease: implicit time, amplitude and oscillatory potentials [Tzekov et al., *Survey of Ophthalmology*, 1999, 44(1): 53-60]. The increment of the implicit time and diminishment of amplitude of the oscillatory potentials (OPs) are also observed in streptozotocin-induced diabetic rats [Hancok et al., *Investigative Ophthalmology & Visual Science*, 2004, 45(3): 1002-1008].

Electroretinography results showed that after 14 days of treatment, the implicit time of the b-wave at 0 db significantly raised compared to pretreatment in the diabetic group (Group 2) (15.5 Right eye; 15.2 Left eye) and did not suffer a significant increased in control group (Group 1) (−2.3 Right eye; −7.5 Left eye) and groups treated with somatostatin composition of example 4 (Group 3) (9.0 Right eye; 4.9 Left eye) or octreotide composition of example 5 (Group 4) (8.8 Right eye; 1.1 Left eye).

Concerning amplitude, somatostatin prevented the diminishment of the b-wave amplitude at −30 db, −10 db and 0 db compared to the diabetic group and octreotide prevented the diminishment of the b-wave amplitude at −30 db but was effective only at the highest dose at −10 db and 0 db.

Figure 2:
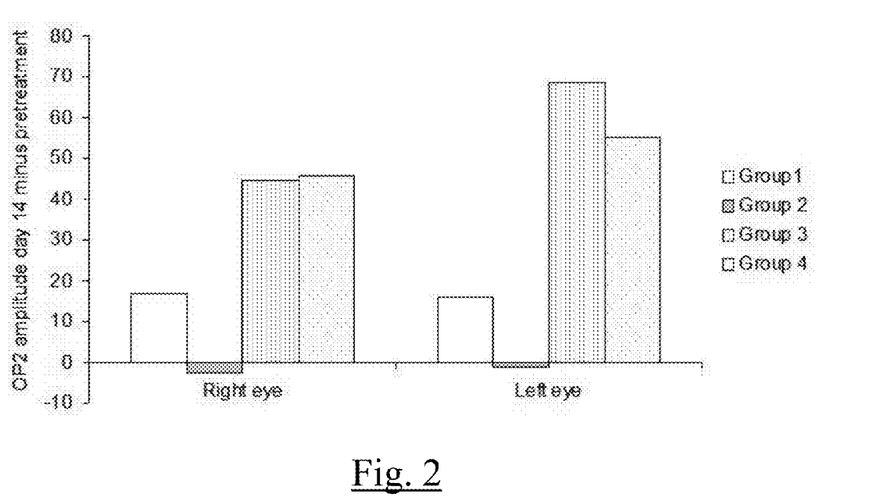
FIG. 2 shows the difference between the amplitude of the second OP in control rats (Group 1); diabetic rats (Group 2); diabetic rats treated with somatostatin (Group 3) and diabetic rats treated with octreotide (Group 4)

The analysis of the oscillatory potentials (OP) of the b-wave at 0 db indicates that somatostatin and octreotide presented a positive effect preventing the diminishment of the amplitude of the second OP (OP2). This effect was already observed on Day 8 and conserved till Day 14. FIG. 2 shows the difference between the amplitude of the second OP in control rats (Group 1: 17.0 Right eye; 15.9 Left eye); diabetic rats (Group 2: −2.5 Right eye; −1.2 Left eye); diabetic rats treated with somatostatin (Group 3: 44.8 Right eye; 68.7 Left eye) and diabetic rats treated with octreotide (Group 4: 45.5 Right eye; 55.1 Left eye).

On day 14, the animals were sacrificed and ocular tissues paraffined. Glial activation and number of apoptotic cells were evaluated as markers of the first step in the development of diabetic retinopathy: retinal neurodegeneration [Carrasco et al., *Diabetes Care;* 2007, 30(11): 1-7].

Figure 3:
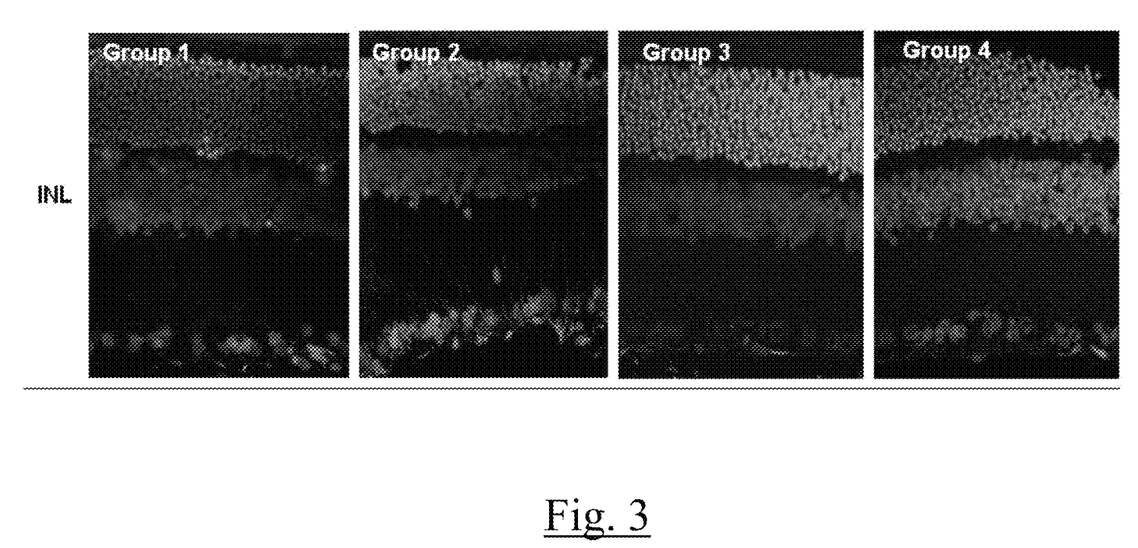
FIG. 3 shows the confocal microscopy images. Confocal GFAP immunohistochemistry 40×. A much higher GFAP expression (brightest labeling) was observed in the ganglion cell layer of STZ-induced diabetic rats (Group 2). Treatment with somatostatin (Group 3) or Octreotide (Group 4) prevented glial cell activation that correlated with GFAP levels similar to the control (Group 1)

Glial activation was determined analysing Glial Fibrillar Protein (GFAP) immunofluorescence by confocal microscopy. Ocular sections of 7 µm thickness were fixed on high adherent coverslips (Visionbiosystems, Newcastle Upon Tyne, UK). They were desparaffined, rehydrated and washed in phosphate buffer saline (PBS). Unspecific unions were blocked incubating the samples for 1 h in PBS 1% BSA (Bovine Serum Albumin) 0.5% Triton X-100. Thereafter, the primary rabbit anti-human GFAP antibody (Sigma, Madrid, Spain) diluted in the blocking buffer (1:100) was incubated for 36 h at 4° C. After three washings for 5 min with PBS, sections were incubated with a secondary antibody anti IgG human labelled with Alexa Fluor® 488 (Invitrogen, Eugene, Oreg.) for 1 h at room temperature. Labelled sections were washed and mounted with fluorescent medium containing 4,6-diamidino-2-phenylindole (DAPI) for staining cell nuclei (Vector Laboratories, Burlingame, Calif.). The sections positives for GFAP were captured in a confocal microscope (FV1000, Olympus. Hamburg, Germany) obtaining optical sections with a 488 nm laser for Alexa 488 and a 405 nm laser for DAPI. GFAP fluorescence was quantified in each image with the Fluoview ASW 1.4 software (Olympus, Hamburg, Germany). Results were normalized to the analysed area (21705.33 µm$^2$). FIG. 3 shows the confocal microscopy images. A higher GFAP expression (brightest labeling) was observed in the ganglion cell layer of STZ-induced diabetic rats (Group 2). Treatment with somatostatin (Group 3) or Octreotide (Group 4) prevented glial cell activation that correlated with GFAP levels similar to the control (Group 1).

The efficacy of the topical ocular treatment with somatostatin (Group 3) and octreotide (Group 4) in the prevention of glial activation provoked by diabetes was determined by GFAP fluorescence values, indicator of glial activation. GFAP fluorescence value was 2095±26 for healthy control Group 1; 6871±159 for Group 2; 2514±90 for Group 3 and 1696±48 for Group 4.

Figure 4:
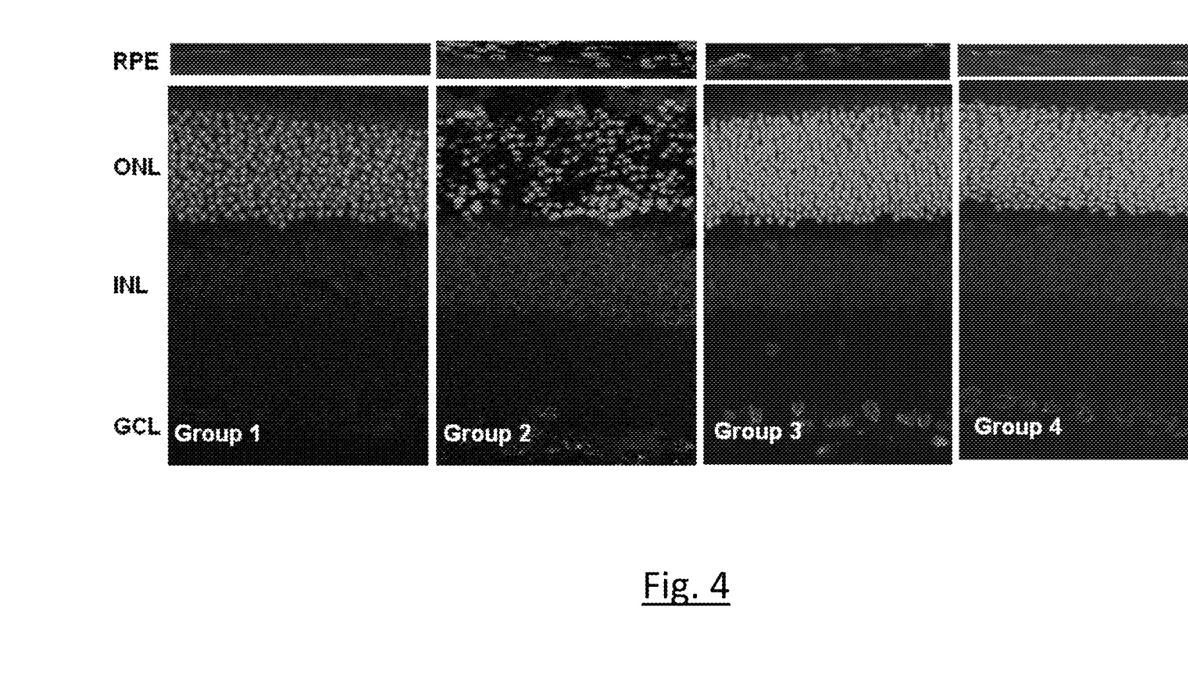
FIG. 4 shows the confocal microscopy images. Confocal images of TUNEL 40×. Retinal degeneration correlated with a higher number of apoptotic cells (brightest labeling means TUNEL positive) specially in the ONL observed in STZ-induced diabetic rats (Group 2). Treatment with somatostatin (Group 3) and octreotide (Group 4) prevented retinal degeneration and showed a similar number of cells that found in healthy control rats (Group 1).

The evaluation of the degree of apoptosis of the retina after 14 days of treatment was done by using the TUNEL ("Terminal Transferase dUTP Nick-End Labeling") technique. The In Situ Cell Death Detection Kit (Roche Diagnostics, Mannheim, Germany) was used. Ocular sections were desparaffined, rehydrated and washed in PBS. Three confocal images (40×) corresponding to a 317.13 µm×317.13 µm surface were obtained for each section. The total number of nuclei and nuclei positive for TUNEL were quantified with the Image J software (http://rsbweb.nih.gov/ij). Staining with propidium iodide (PI) was done for examining the nucleus morphology and discard false positives. FIG. 4 shows the confocal microscopy images. Retinal degeneration correlated with a higher number of apoptotic cells (brightest labeling means TUNEL positive) observed in streptozotocin-induced diabetic rats (Group 2). Treatment with somatostatin (Group 3) and octreotide (Group 4) prevented retinal degeneration and showed a similar number of cells that found in healthy control rats (Group 1).

Table 2 shows the percentage of apoptotic cells respect to the total number of cells in different retinal layers such as retinal pigment epithelium (RPE), outer nuclear layer (ONL), inner nuclear layer (INL) and ganglion cell layer (GCL). The increment in the percentage of apoptotic cells is significant in diabetic rats (Group 2). Topical ocular treatment with somatostatin (Group 3) or octreotide (Group 4) reduced the number of apoptotic cells till control levels (Group 1).

TABLE 2

| | Percentage of apoptotic cells % Apoptotic cells | | | |
|---|---|---|---|---|
| | RPE | ONL | INL | GCL |
| Group 1 | 6 | 2 | 0 | 9 |
| Group 2 | 28 | 10 | 4 | 35 |
| Group 3 | 6 | 3 | 1 | 14 |
| Group 4 | 11 | 5 | 0.1 | 7 |

Neurodegeneration of retinal cells is one of the first steps in the development of diabetic retinopathy. The results of electroretinography, glial activation and apoptosis indicated that topical ocular administration of somatostatin or octreotide for 14 days prevented retinal degeneration in streptozotocin-induced diabetic rats.

The invention claimed is:

1. A method of treatment of a posterior segment of eye disease selected from the group consisting of nonproliferative diabetic retinopathy, proliferative diabetic retinopathy, retinal neurodegeneration, retinal neovascularization, ischemia-induced retinopathy, retinopathy of prematurity, sickle-cell retinopathy, retinal vein occlusion, retinitis pigmentosa and combinations thereof, comprising:
   administering topically a therapeutically effective amount of somatostatin or a somatostatin analogue selected from the group consisting of somatostatin-28, somatostatin-14, somatostatin-13, prosomatostatin, octreotide, lanreotide, vapreotide, pasireotide, seglitide, cortistatin, and pharmaceutically acceptable salts thereof, by a topical ophthalmic composition selected from the group consisting of eye drops, ointments and unguents, wherein the concentration of the somatostatin or somatostatin analogue ranges between 1 μg/mL and 40 mg/mL, and wherein the composition is an isotonic aqueous solution, a poly(vinyl alcohol) aqueous solution, or mixtures thereof of pH between 3 and 8.

2. The method according to claim 1, wherein the somatostatin or somatostatin analogue is substituted with an acyl group or a polyethylene glycol moiety.

3. The method according to claim 1, wherein the concentration ranges between 1 μg/mL and 10 mg/mL.

4. The method according to claim 1, wherein the ophthalmic composition further comprises a preservative.

5. The method according to claim 4, wherein the preservative is selected from the group consisting of benzalkonium chloride, benzoic acid, alkyl parabens, alkyl benzoates, chlorobutanol, chlorocresol, cetyl alcohols, fatty alcohols, hexadecyl alcohol, organometallic compounds of mercury, mercury acetate, phenylmercury nitrate or borate, diazolidinyl urea, diisopropyl adipate, dimethyl polysiloxane, salts of EDTA, vitamin E and mixtures thereof.

6. The method according to claim 1, wherein the ophthalmic composition further comprises an agent that increases permeability of the somatostatin or somatostatin analogue.

7. The method according to claim 6, wherein the agent that increases permeability is selected from the group consisting of benzalkonium chloride, saponins, fatty acids, polyoxyethylene fatty ethers, alkyl esters of fatty acids, pyrrolidones, polyvinylpyrrolidone, pyruvic acids, pyroglutamic acids, and mixtures thereof.

8. The method according to claim 1, wherein the somatostatin or somatostatin analogue is incorporated in liposomes, mixed liposomes, niosomes, ethosomes, nanoparticles, solid lipid nanoparticles, nanostructured lipid carriers, micelles, mixed micelles of surfactants, surfactant-phospholipid mixed micelles, nanospheres, liposphere and/or nanocapsules.

9. The method according to claim 1, wherein the treatment of posterior segment of eye diseases benefits from binding of somatostatin or somatostatin analogue to somatostatin receptors.

* * * * *